(12) United States Patent
Wollrab et al.

(10) Patent No.: US 8,772,553 B2
(45) Date of Patent: Jul. 8, 2014

(54) HYDROGENATION REACTION CONDITIONS FOR PRODUCING ETHANOL

(71) Applicant: Celanese International Corporation, Irving, TX (US)

(72) Inventors: Radmila Wollrab, Pasadena, TX (US); Victor J. Johnston, Houston, TX (US); Heiko Weiner, Pasadena, TX (US)

(73) Assignee: Celanese International Corporation, Irvine, TX (US)

( * ) Notice: Subject to any disclaimer, the term of this patent is extended or adjusted under 35 U.S.C. 154(b) by 81 days.

(21) Appl. No.: 13/661,550

(22) Filed: Oct. 26, 2012

(65) Prior Publication Data

US 2014/0121422 A1    May 1, 2014

(51) Int. Cl.
*C07C 29/149*    (2006.01)

(52) U.S. Cl.
CPC .................................. *C07C 29/149* (2013.01)
USPC .......................................... 568/885; 268/885

(58) Field of Classification Search
CPC .................................................... C07C 29/149
USPC ........................................................ 568/885
See application file for complete search history.

(56) References Cited

U.S. PATENT DOCUMENTS

| | | |
|---|---|---|
| 2,549,416 A | 4/1951 | Brooks |
| 2,607,807 A | 8/1952 | Ford |
| 2,744,939 A | 5/1956 | Kennel |
| 2,882,244 A | 4/1959 | Milton |
| 3,130,007 A | 4/1964 | Breck |
| 3,361,769 A | 1/1968 | Halpern et al. |
| 3,383,311 A | 5/1968 | Groszek |
| 3,478,112 A | 11/1969 | Karl et al. |
| 3,531,543 A | 9/1970 | Clippinger et al. |
| 3,702,886 A | 11/1972 | Argauer et al. |
| 3,729,429 A | 4/1973 | Robson |
| 3,864,284 A | 2/1975 | Clippinger et al. |
| 3,953,524 A | 4/1976 | Steiner |
| 3,981,923 A | 9/1976 | Stouthamer et al. |
| 4,048,096 A | 9/1977 | Bissot |
| 4,065,512 A | 12/1977 | Cares |
| 4,199,438 A | 4/1980 | Antos |
| 4,317,918 A | 3/1982 | Takano et al. |
| 4,337,351 A | 6/1982 | Larkins, Jr. |
| 4,374,265 A | 2/1983 | Larkins, Jr. |
| 4,395,576 A | 7/1983 | Kwantes et al. |
| 4,398,039 A | 8/1983 | Pesa et al. |
| 4,399,305 A | 8/1983 | Schreck |
| 4,421,939 A | 12/1983 | Kiff et al. |
| 4,426,541 A | 1/1984 | King |
| 4,443,639 A | 4/1984 | Pesa et al. |
| 4,456,775 A | 6/1984 | Travers et al. |
| 4,476,326 A | 10/1984 | Lin et al. |
| 4,480,115 A | 10/1984 | McGinnis |
| 4,514,515 A | 4/1985 | Travers et al. |
| 4,514,521 A | 4/1985 | Smith |
| 4,517,391 A | 5/1985 | Schuster et al. |
| 4,521,630 A | 6/1985 | Wattimena et al. |
| 4,550,185 A | 10/1985 | Mabry et al. |
| 4,600,571 A | 7/1986 | McCarroll et al. |
| 4,628,130 A | 12/1986 | Bournonville et al. |
| 4,678,543 A | 7/1987 | Houben et al. |
| 4,692,218 A | 9/1987 | Houben et al. |
| 4,760,171 A | 7/1988 | Isogai et al. |
| 4,777,303 A | 10/1988 | Kitson et al. |
| 4,804,791 A | 2/1989 | Kitson et al. |
| 4,826,795 A | 5/1989 | Kitson et al. |
| 4,837,368 A | 6/1989 | Gustafson et al. |
| 4,880,937 A | 11/1989 | Matsushita et al. |
| 4,943,354 A | 7/1990 | Osterburg et al. |
| 4,985,572 A | 1/1991 | Kitson et al. |
| 4,990,655 A | 2/1991 | Kitson et al. |
| 5,008,235 A | 4/1991 | Wegman et al. |
| 5,061,671 A | 10/1991 | Kitson et al. |
| 5,137,861 A | 8/1992 | Shih et al. |
| 5,149,680 A | 9/1992 | Kitson et al. |
| 5,155,084 A | 10/1992 | Horn et al. |
| 5,185,476 A | 2/1993 | Gustafson |
| 5,243,095 A | 9/1993 | Roberts et al. |
| 5,292,704 A | 3/1994 | Lester |
| 5,292,916 A | 3/1994 | Matsuzaki et al. |
| 5,334,769 A | 8/1994 | Ferrero et al. |
| 5,350,504 A | 9/1994 | Dessau |
| 5,391,291 A | 2/1995 | Winquist et al. |
| 5,426,246 A | 6/1995 | Nagahara et al. |

(Continued)

FOREIGN PATENT DOCUMENTS

| | | |
|---|---|---|
| CN | 1230458 | 10/1999 |
| CN | 102228831 | 11/2011 |

(Continued)

OTHER PUBLICATIONS

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

(Continued)

*Primary Examiner* — Elvis O Price

(57) ABSTRACT

The present invention relates to processes for producing ethanol from a feed stream comprising hydrogen and acetic acid and/or ethyl acetate. The reaction occurs at a temperature greater than 225° C. and the feed stream has a liquid hourly space velocity of at least 0.2 hr$^{-1}$. The reaction occurs in the presence of a catalyst comprising a precious metal and one or more active metals on a modified support.

20 Claims, 4 Drawing Sheets

(56) References Cited

U.S. PATENT DOCUMENTS

| | | | |
|---|---|---|---|
| 5,476,827 A | 12/1995 | Ferrero et al. |
| RE35,377 E | 11/1996 | Steinberg et al. |
| 5,585,523 A | 12/1996 | Weiguny et al. |
| 5,719,097 A | 2/1998 | Chang et al. |
| 5,767,307 A | 6/1998 | Ramprasad et al. |
| 5,821,111 A | 10/1998 | Grady et al. |
| 5,849,657 A | 12/1998 | Rotgerink et al. |
| 5,861,530 A | 1/1999 | Atkins et al. |
| 5,945,570 A | 8/1999 | Arhancet et al. |
| 5,955,397 A | 9/1999 | Didillon et al. |
| 5,977,010 A | 11/1999 | Roberts et al. |
| 6,040,474 A | 3/2000 | Jobson et al. |
| 6,046,127 A | 4/2000 | Mimoun |
| 6,049,008 A | 4/2000 | Roberts et al. |
| 6,093,845 A | 7/2000 | Van Acker et al. |
| 6,114,571 A | 9/2000 | Abel et al. |
| 6,121,498 A | 9/2000 | Tustin et al. |
| 6,204,417 B1 | 3/2001 | Fischer et al. |
| 6,232,352 B1 | 5/2001 | Vidalin |
| 6,232,504 B1 | 5/2001 | Barteau et al. |
| 6,281,160 B1 | 8/2001 | Basset et al. |
| 6,294,703 B1 | 9/2001 | Hara et al. |
| 6,462,231 B1 | 10/2002 | Yanagawa et al. |
| 6,462,244 B1 | 10/2002 | Huang et al. |
| 6,472,555 B2 | 10/2002 | Choudary et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,509,290 B1 | 1/2003 | Vaughn et al. |
| 6,524,993 B2 | 2/2003 | Yamaguchi et al. |
| 6,559,333 B1 | 5/2003 | Brunelle et al. |
| 6,603,038 B1 | 8/2003 | Hagemeyer et al. |
| 6,632,330 B1 | 10/2003 | Colley et al. |
| 6,657,078 B2 | 12/2003 | Scates et al. |
| 6,670,490 B1 | 12/2003 | Campos et al. |
| 6,685,754 B2 | 2/2004 | Kindig et al. |
| 6,693,213 B1 | 2/2004 | Kolena et al. |
| 6,696,596 B1 | 2/2004 | Herzog et al. |
| 6,727,380 B2 | 4/2004 | Ellis et al. |
| 6,765,110 B2 | 7/2004 | Warner et al. |
| 6,768,021 B2 | 7/2004 | Horan et al. |
| 6,809,217 B1 | 10/2004 | Colley et al. |
| 6,812,372 B2 | 11/2004 | Janssen et al. |
| 6,852,877 B1 | 2/2005 | Zeyss et al. |
| 6,903,045 B2 | 6/2005 | Zoeller et al. |
| 6,906,228 B2 | 6/2005 | Fischer et al. |
| 6,927,048 B2 | 8/2005 | Verser et al. |
| 6,987,200 B2 | 1/2006 | Hagemeyer et al. |
| 7,074,603 B2 | 7/2006 | Verser et al. |
| 7,084,312 B1 | 8/2006 | Huber et al. |
| 7,297,236 B1 | 11/2007 | Vander Griend et al. |
| 7,335,800 B2 | 2/2008 | Komplin et al. |
| 7,341,706 B2 | 3/2008 | Fuglerud et al. |
| 7,351,559 B2 | 4/2008 | Verser et al. |
| 7,375,049 B2 | 5/2008 | Hayes et al. |
| 7,425,657 B1 | 9/2008 | Elliott et al. |
| 7,507,562 B2 | 3/2009 | Verser et al. |
| 7,538,060 B2 | 5/2009 | Barnicki et al. |
| 7,553,397 B1 | 6/2009 | Colley et al. |
| 7,572,353 B1 | 8/2009 | Vander et al. |
| 7,608,744 B1 | 10/2009 | Johnston et al. |
| 7,682,812 B2 | 3/2010 | Verser et al. |
| 7,790,938 B2 | 9/2010 | Kawasaki et al. |
| 7,820,852 B2 | 10/2010 | Johnston et al. |
| 7,842,844 B2 | 11/2010 | Atkins |
| 7,847,134 B2 | 12/2010 | Lee et al. |
| 7,863,489 B2 | 1/2011 | Johnston et al. |
| 7,884,253 B2 | 2/2011 | Stites et al. |
| 7,888,082 B2 | 2/2011 | Verser et al. |
| 7,923,405 B2 | 4/2011 | Kharas et al. |
| 7,964,379 B2 | 6/2011 | Verser et al. |
| 8,071,389 B2 | 12/2011 | Weck et al. |
| 8,071,821 B2 | 12/2011 | Johnston et al. |
| 8,080,693 B2 | 12/2011 | Chornet et al. |
| 8,088,832 B2 | 1/2012 | Melnichuk et al. |
| 8,173,324 B2 | 5/2012 | Fisher et al. |
| 8,232,440 B2 | 7/2012 | Holtzapple et al. |
| 8,288,596 B2 | 10/2012 | Garton et al. |
| 8,299,132 B2 | 10/2012 | Gracey et al. |
| 8,309,782 B2 | 11/2012 | Le Peltier et al. |
| 8,329,961 B2 | 12/2012 | Danjo et al. |
| 2003/0077771 A1 | 4/2003 | Verser et al. |
| 2003/0104587 A1 | 6/2003 | Verser et al. |
| 2003/0105171 A1 | 6/2003 | Subramanian et al. |
| 2006/0019360 A1 | 1/2006 | Verser et al. |
| 2006/0102520 A1 | 5/2006 | Lapinski et al. |
| 2006/0127999 A1 | 6/2006 | Verser et al. |
| 2007/0238605 A1 | 10/2007 | Strehlau et al. |
| 2008/0207953 A1 | 8/2008 | Houssin et al. |
| 2008/0257784 A1 | 10/2008 | Dath et al. |
| 2009/0023192 A1 | 1/2009 | Verser et al. |
| 2009/0166172 A1 | 7/2009 | Casey et al. |
| 2009/0221725 A1 | 9/2009 | Chorney et al. |
| 2009/0326080 A1 | 12/2009 | Chornet et al. |
| 2010/0029995 A1 | 2/2010 | Johnston et al. |
| 2010/0121114 A1 | 5/2010 | Johnston et al. |
| 2010/0197985 A1 | 8/2010 | Johnston et al. |
| 2010/0249479 A1 | 9/2010 | Berg-Slot et al. |
| 2011/0004034 A1 | 1/2011 | Daniel et al. |
| 2011/0046421 A1 | 2/2011 | Daniel et al. |
| 2011/0060169 A1 | 3/2011 | Kaizik et al. |
| 2011/0060174 A1 | 3/2011 | Studt et al. |
| 2011/0082322 A1 | 4/2011 | Jevtic et al. |
| 2011/0224462 A1 | 9/2011 | Ditzel et al. |

FOREIGN PATENT DOCUMENTS

| | | |
|---|---|---|
| CN | 102229520 | 11/2011 |
| EP | 0104197 | 4/1984 |
| EP | 0137749 | 4/1985 |
| EP | 0175558 | 3/1986 |
| EP | 0192587 | 8/1986 |
| EP | 0400904 | 5/1990 |
| EP | 0372847 | 6/1990 |
| EP | 0408528 | 7/1990 |
| EP | 0407038 | 1/1991 |
| EP | 0653242 | 5/1995 |
| EP | 2060553 | 5/2009 |
| JP | 6-116182 | 4/1994 |
| JP | 10-306047 | 11/1998 |
| JP | 11-147845 | 6/1999 |
| JP | 2001-046874 | 2/2001 |
| JP | 2001-157841 | 6/2001 |
| WO | WO 83/03409 | 10/1983 |
| WO | WO 2009/009322 | 1/2009 |
| WO | WO 2009/009323 | 1/2009 |

OTHER PUBLICATIONS

ZeaChem, Inc., Technology Overview, Lakewood, Colorado www.zeachem.com, 2008.

T. Yokoyama, et al., "Carboxylic Acids and Derivatives", Fine Chemicals through Heterogenous Catalysis, pp. 370-379.

Xiang, et al., "XPS study of potassium-promoted molybdenum carbides for mixed alcohols synthesis via CO hydrogenation", Journal of Natural Gas Chemistry, vol. 19, 2010, pp. 151-155.

Subramani et al. "A Review of Recent Literature to Search for an Efficient Catalytic Process for the Conversion of Syngas to Ethanol," Energy & Fuels, 2008, vol. 22, pp. 814-839.

Spivey et al., "Heterogeneous catalytic synthesis of ethanol from biomass-dervied syngas," Chemical Society Review, 2007, vol. 36, pp. 1514-1528.

Santori et al.(2000). Hydrogenation of carbonylic compounds on Pt/SiO2 catalysts modified with SnBu4, Studies in Surface Science and Catalysis, 130, 2063-2068.

Rodrigues and Bueno, "Co/SiO2 catalysts for selective hydrogenation of crotonaldehyde: III. Promoting effect of zinc," Applied Catalysis A: General (2004), 257, p. 210-211.

A. Rehmat et al., "Selective Methanation of Carbon Monoxide" Ind. Eng. Chem. Prod. Res. Develop., vol. 9 , No. 4, pp. 512-515 (1970).

Rachmady, Acetic Acid Reduction by H2 on Bimetallic Pt—Fe Catalysts, Journal of Catalysis 209, 87-98 (Apr. 1, 2002), Elsevier Science (USA).

(56) References Cited

OTHER PUBLICATIONS

Pestman et al., The formation of ketones and aldehydes from carboxylic acids, structure-activity relationship for two competitive reactions, Journal of Molecular Catalysis A: Chemical 103 Jun. 14, 1995, 175-180.

Pestman et al., Reactions of Carboxylic Acids on Oxides, Journal of Catalysis 168:255-264 (1997).

Pestman et al., Identification of the Active Sites in the Selective Hydrogenation of Acetic Acid to Acetaldehyde on Iron Oxide Catalysts, Journal of Catalysis 174:142-152 (1998).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Ordóñez et al., The role of metal and support sites on the hydrogenation of acetic acid on Ru-based catalysts, 21st NAM San Francisco, CA, Jun. 10, 2009.

Nitta, et al. "Selective hydrogenation of $\alpha\beta$-unsaturated aldehydes on cobalt—silica catalysts obtained from cobalt chrysotile," Applied Catal. (1989), 56, p. 9-22.

Nefedov and I V Mishin B K, "Synthesis of diethyl ether in presence of zeolite catalysts", Russian Chem. Bull., Springer Anew York LLC, v. 28, Jan. 1, 1979, pp. 183-186.

Liberkova, and Tourounde, "Performance of Pt/SnO2 catalyst in the gas phase hydrogenation of crotonaldehyde," J. Mol. Catal. A: Chemical (2002), 180, p. 221-230.

Jingfa D et al., "Acidic properties of ZSM-5 zeolite and conversion of ethanol to diethyl ether," Applied Catalyst, v. 41, Jan. 1, 1988, pp. 13-22.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Consonni, et al. "High Performances of Pt/ZnO Catalysts in Selective Hydrogenation of Crotonaldehyde," J. Catal. (1999), 188, p. 165-175.

Ammari, et al. "An emergent catalytic material: Pt/ZnO catalyst for selective hydrogenation of crotonaldehyde," J. Catal. (2004), 221, p. 32-42.

Ammari, et al. "Selective hydrogenation of crotonaldehyde on Pt/ZnCl2/SiO2 catalysts," J. Catal. (2005), 235, p. 1-9.

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

Proc. Roy Soc. A314, pp. 473-498 (1970).

Brunauer Emmett and Teller, J. Am. Chem. Soc. 60, 309 (1938).

HYDROGENATION REACTION CONDITIONS FOR PRODUCING ETHANOL

FIELD OF THE INVENTION

The present invention relates to processes for producing ethanol from a feed stream comprising a carboxylic acid and/or esters thereof in the presence of the hydrogenation catalysts. In particular, the present invention relates to a process for producing ethanol from a feed stream with a temperature of greater than 225° C. and a liquid hourly space velocity (LHSV) of at least 0.2 $hr^{-1}$.

BACKGROUND OF THE INVENTION

Ethanol for industrial use is conventionally produced from petrochemical feed stocks, such as oil, natural gas, or coal, from feed stock intermediates, such as syngas, or from starchy materials or cellulosic materials, such as corn or sugar cane. Conventional methods for producing ethanol from petrochemical feed stocks, as well as from cellulosic materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulosic material, are converted to ethanol by fermentation. However, fermentation is typically used for consumer production of ethanol, which is suitable for fuels or human consumption. In addition, fermentation of starchy or cellulosic materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. The reduction of various carboxylic acids over metal oxides has been proposed by EP0175558 and U.S. Pat. No. 4,398,039. A summary some of the developmental efforts for hydrogenation catalysts for conversion of various carboxylic acids is provided in Yokoyama, et al., "Carboxylic acids and derivatives" in: *Fine Chemicals Through Heterogeneous Catalysis,* 2001, 370-379.

U.S. Pat. No. 6,495,730 describes a process for hydrogenating carboxylic acid using a catalyst comprising activated carbon to support active metal species comprising ruthenium and tin. U.S. Pat. No. 6,204,417 describes another process for preparing aliphatic alcohols by hydrogenating aliphatic carboxylic acids or anhydrides or esters thereof or lactones in the presence of a catalyst comprising Pt and Re. U.S. Pat. No. 5,149,680 describes a process for the catalytic hydrogenation of carboxylic acids and their anhydrides to alcohols and/or esters in the presence of a catalyst containing a Group VIII metal, such as palladium, a metal capable of alloying with the Group VIII metal, and at least one of the metals rhenium, tungsten or molybdenum. U.S. Pat. No. 4,777,303 describes a process for the productions of alcohols by the hydrogenation of carboxylic acids in the presence of a catalyst that comprises a first component which is either molybdenum or tungsten and a second component which is a noble metal of Group VIII on a high surface area graphitized carbon. U.S. Pat. No. 4,804,791 describes another process for the production of alcohols by the hydrogenation of carboxylic acids in the presence of a catalyst comprising a noble metal of Group VIII and rhenium. U.S. Pat. No. 4,517,391 describes preparing ethanol by hydrogenating acetic acid under superatmospheric pressure and at elevated temperatures by a process wherein a predominantly cobalt-containing catalyst.

Existing processes suffer from a variety of issues impeding commercial viability including: (i) catalysts without requisite selectivity to ethanol; (ii) catalysts which are possibly prohibitively expensive and/or nonselective for the formation of ethanol and that produce undesirable by-products; (iii) required operating temperatures and pressures which are excessive; (iv) insufficient catalyst life; and/or (v) required activity for both ethyl acetate and acetic acid.

SUMMARY OF THE INVENTION

In a first embodiment, the invention is directed to a process for producing ethanol, comprising contacting hydrogen with a feed stream comprising acetic acid and/or ethyl acetate in a reactor at a temperature greater than 225° C. in the presence of a catalyst, under conditions effective to form ethanol, provided that the liquid hourly space velocity (LHSV) of the feed stream to the reactor may be from 0.2 $hr^{-1}$ to 1 $hr^{-1}$, preferably from 0.2 $hr^{-1}$ to 0.8 $hr^{-1}$, wherein the catalyst comprises a precious metal and one or more active metals on a modified support, wherein the modified support comprises (i) support material, and (ii) a support modifier comprising a metal selected from the group consisting of tungsten, molybdenum, vanadium, niobium and tantalum, and further wherein the one or more active metals are selected from the group consisting of copper, iron, cobalt, vanadium, nickel, titanium, zinc, chromium, molybdenum, tungsten, tin, lanthanum, cerium, manganese and mixtures thereof. In some embodiments, the temperature may be from 250° C. to 300° C. and the LHSV of the feed stream fed to the reactor may be from 0.2 to 1 $hr^{-1}$. Selectivity of acetic acid to ethanol may be greater than 60%. In further embodiments, the temperature may be at least 250° C., the LHSV of the feed stream fed to the reactor may be at least 0.3 $hr^{-1}$, e.g., from 0.3 to 1 $hr^{-1}$, and conversion of acetic acid may be at least 60%. In other embodiments, the temperature may be at least 275° C., the LHSV of the feed stream fed to the reactor may be at least 0.3 $hr^{-1}$, e.g., from 0.3 to 1 $hr^{-1}$, and conversion of acetic acid may be at least 80%. In another embodiment, the temperature may be at least 300° C., the LHSV of the feed stream fed to the reactor may be at least 0.3 $hr^{-1}$, e.g., from 0.3 to 1 $hr^{-1}$, and conversion of acetic acid may be at least 85%.

In some embodiments, the precious metal may be selected from the group consisting of rhodium, rhenium, ruthenium, platinum, palladium, osmium, iridium and gold and the one or more active metals may comprise cobalt and tin. In some embodiments, the precious metal may be present in an amount from 0.1 to 5 wt. %, and the one or more active metals comprise a second metal and a third metal, wherein the second metal may be present in an amount from 0.5 to 20 wt. % and the third metal may be present in an amount from 0.5 to 20 wt. %, based on the total weight of the catalyst. In other embodiments, the precious metal may be platinum and the one or more active metals may comprise cobalt and tin. The platinum may be present in an amount from 0.1 to 5 wt. %, the cobalt may be present in an amount from 0.5 to 20 wt. % and the tin may be present in an amount from 0.5 to 20 wt. %, based on the total weight of the catalyst. In some embodiments, the precious metal may be palladium and the one or more active metals may comprise cobalt and tin. The palladium may be present in an amount from 0.1 to 5 wt. %, the cobalt may be present in an amount from 0.5 to 20 wt. % and the tin may be present in an amount from 0.5 to 20 wt. %, based on the total weight of the catalyst.

In some embodiments, the support modifier may comprise tungsten oxide. In other embodiments, the support modifier may comprise tungsten as a tungstate of cobalt. The support material may be selected from the group consisting of silica, alumina, titania, silica/alumina, pyrogenic silica, high purity silica, zirconia, carbon, zeolites and mixtures thereof. The acetic acid is derived from a carbonaceous material selected from the group consisting of oil, coal, natural gas and biomass.

In a second embodiment, the invention is directed to a process for producing ethanol comprising contacting hydrogen with a mixed feed stream comprising from 40 to 95 wt. % acetic acid and 5 to 60 wt. % ethyl acetate in a reactor at a temperature from greater than 225° C. to 300° C. in the presence of a catalyst, wherein the liquid hourly space velocity of the feed stream to the reactor is from 0.2 hr$^{-1}$ to 1 hr$^{-1}$, to form ethanol and achieve steady state ethyl acetate concentration, wherein the catalyst comprises a precious metal and one or more active metals on a modified support, wherein the modified support comprises (i) support material, and (ii) a support modifier comprising a metal selected from the group consisting of tungsten, molybdenum, vanadium, niobium and tantalum, and further wherein the one or more active metals are selected from the group consisting of copper, iron, cobalt, vanadium, nickel, titanium, zinc, chromium, molybdenum, tungsten, tin, lanthanum, cerium, manganese and mixtures thereof. In feed streams that comprise both acetic acid and ethyl acetate, it is preferred to achieve a state of ethyl acetate concentration which means that the amount of ethyl acetate feed to the reactor is substantial similar to the amount of ethyl acetate in the crude ethanol product.

BRIEF DESCRIPTION OF THE DRAWINGS

The present invention will be better understood in view of the appended non-limiting figures, in which.

DETAILED DESCRIPTION OF THE INVENTION

Figure 1:
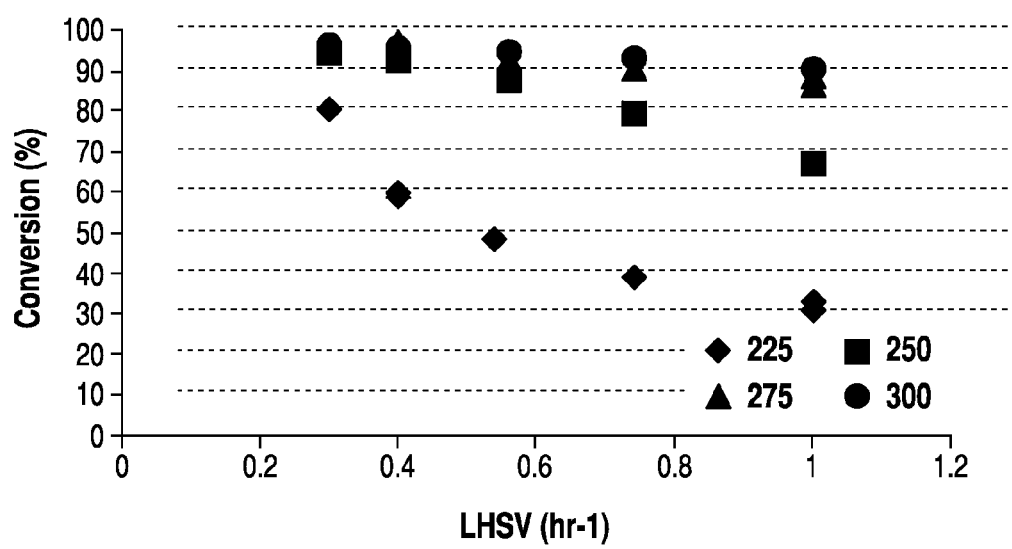
FIG. 1 shows acetic acid conversion for one embodiment of the present invention.

The present invention relates to processes for recovering ethanol produced by hydrogenating a feed stream comprising a carboxylic acid, e.g., acetic acid, and/or an ester thereof, in the presence of a catalyst. The catalyst comprises a precious metal and one or more active metals on a modified support, wherein the modified support comprises (i) support material, and (ii) a support modifier comprising a metal selected from the group consisting of tungsten, molybdenum, vanadium, niobium and tantalum. The one or more active metals are selected from the group consisting of copper, iron, cobalt, vanadium, nickel, titanium, zinc, chromium, molybdenum, tungsten, tin, lanthanum, cerium, manganese and mixtures thereof. In one embodiment, the catalyst comprises platinum, tin and cobalt on a silicaceous support modified by cobalt, tin and tungsten. In another embodiment, the catalyst comprises platinum and tin on a silicaceous support modified by tungsten and cobalt. In yet another embodiment, the catalyst comprises platinum, tin and cobalt on a silicaceous support modified by tungsten. The hydrogenation reaction produces a crude ethanol stream that comprises ethanol, water, ethyl acetate, acetaldehyde, and other impurities. The processes of the present invention minimize selectivity to ethyl acetate by controlling the reaction temperature and/or the LHSV of the feed stream.

For purposes of the present invention, the term "conversion" refers to the amount of acetic acid or mixtures of acetic acid and ethyl acetate that are converted to a compound other than acetic acid or ethyl acetate, respectively. For feed streams of pure acetic acid that comprise no ethyl acetate, the acetic acid conversion may be at least 60%, e.g., at least 75%, at least 90%, or at least 95%. Very high conversions of greater than 99% may also be achieved. For feed streams of acetic acid and ethyl acetate, the acetic conversion is similarly at least 60%, and the process is effective for consuming ethyl acetate at a rate sufficiently great so as to at least offset the rate of ethyl acetate production, thereby resulting in a non-negative ethyl acetate conversion, i.e., no net increase in ethyl acetate is realized. For example, an ethyl acetate conversion that is effectively 0% or that is greater than 0%. In some embodiments, the processes of the invention are effective in providing ethyl acetate conversions of at least 0%, e.g., at least 5%, at least 10%, at least 15%, at least 20%, or at least 35%. This results in an overall low selectivity to ethyl acetate for feed streams of mixtures of acetic acid and ethyl acetate.

In continuous processes, the ethyl acetate being added, through a fresh or recycled stream, to the hydrogenation reactor and ethyl acetate leaving the reactor in the crude product preferably approaches a certain level after the process reaches equilibrium. In preferred embodiments, the concentration of ethyl acetate in the mixed feed and crude product is less than 40 wt. %, less than 25 wt. % or less than 15 wt. %, after equilibrium has been achieved. In preferred embodiments, the process forms a crude product comprising ethanol and ethyl acetate, and the crude product has an ethyl acetate steady state concentration from 0.1 to 40 wt. %, e.g., from 0.1 to 20 wt. % or from 0.1 to 15 wt. %.

Selectivity is expressed as a mole percent based on converted acetic acid. It should be understood that each compound converted from acetic acid and/or ethyl acetate has an independent selectivity and that selectivity is independent of conversion. For example, if 60 mole % of the converted acetic acid is converted to ethanol, we refer to the ethanol selectivity as 60%. For purposes of the present invention, the total selectivity is based on the converted acetic acid for pure feed streams and based on the combined converted acetic acid and ethyl acetate for mixed stream. Preferably, total selectivity to ethanol is at least 60%, e.g., at least 70%, or at least 80%, at least 85% or at least 88%.

In one embodiment, the present invention is related to a process for producing ethanol, comprising contacting a feed stream comprising hydrogen, acetic acid and/or ethyl acetate in a reactor in the presence of the above described catalyst, under conditions effective to form ethanol. The temperature in the reactor is greater than 225° C., preferably from greater than 225° C. to 300° C., and the LHSV of the feed stream to the reactor is from 0.2 to 1 hr$^{-1}$. Operating above 1 hr$^{-1}$ with the catalysts of the present invention tends to provide an undesirable increase in ethyl acetate selectivity and decrease in acetic acid conversion. At temperatures greater than 225° C. as the LHSV decreases the selectivity to ethyl acetate also decreases. This is surprising because at temperatures of 225° C. or below, the trend of ethyl acetate selectivity is the opposite. Also, catalysts having a calcium-containing support modifier demonstrate a similar trend of decreasing ethyl acetate selectivity at higher LHSV regardless of temperature. The problem with decreasing ethyl acetate at temperatures of 225° C. and below and using a catalyst that comprises calcium is that conversion of ethyl acetate decreases at higher LHSV.

In terms of ranges, the temperature in the reactor may range from 250 to 300° C. and the LHSV, may range from 0.2 to 1 hr$^{-1}$, e.g., from 0.2 to 0.8 hr$^{-1}$. The selectivity of acetic acid to ethyl acetate may be less than 30%, e.g., less than 25%, less than 20% or less than 15%. Under mixed feed conditions, where acetic acid and ethyl acetate are fed to the reactor, it is preferred to achieve steady-state conditions of ethyl acetate concentrations. Thus, the selectivity of the mixed fed to ethyl acetate is preferably less than 5%, less than 0% or less than −5%.

It has surprisingly and unexpectedly been discovered that by controlling the temperature and LHSV of the feed stream, conversion of acetic acid may be maintained at above 60% while selectivity of acetic acid to ethyl acetate may be minimized to below 30%. Specifically, it was surprising and unexpected that by raising the temperature above 225° C., the selectivity of acetic acid to ethyl acetate decreased as LHSV decreased. This was surprising because as LHSV decreases, residence time of the feed stream in the reactor increases, which would be expected to result in increased selectivity to ethyl acetate.

In some embodiments, the temperature in the reactor is at least 250° C. and the LHSV of the feed stream is at least 0.3 hr$^{-1}$. The LHSV may range from 0.3 hr$^{-1}$ to 1 hr$^{-1}$, e.g., from 0.3 hr$^{-1}$ to 0.8 hr$^{-1}$ or from 0.3 hr$^{-1}$ to 0.6 hr$^{-1}$. Under these conditions, when acetic acid is fed to the reactor, acetic acid conversion may be at least 60%, e.g., at least 70%, at least 80% or at least 90%. The selectivity to ethyl acetate may be less than 30%, e.g., less than 27.5% or less than 25%. When a mixed feed stream comprising acetic acid and ethyl acetate is fed to the reactor under the above temperature and LHSV conditions, acetic acid conversion may be at least 70%, e.g., at least 80% or at least 90%. The selectivity to ethyl acetate may be less than 35%, e.g., less than 30%, less than 25%, less than 20% or less than 15%.

In other embodiments, the temperature in the reactor is at least 275° C. and the LHSV of the feed stream is at least 0.3 hr$^{-1}$. The LHSV may range from 0.3 hr$^{-1}$ to 1 hr$^{-1}$, e.g., from 0.3 hr$^{-1}$ to 0.8 hr$^{-1}$ or from 0.3 hr$^{-1}$ to 0.6 hr$^{-1}$. Under these conditions, when acetic acid is fed to the reactor, acetic acid conversion may be at least 80%, e.g., at least 85%, or at least 90%. The selectivity to ethyl acetate may be less than 30%, e.g., less than 27.5% or less than 25%. When a mixed feed stream comprising acetic acid and ethyl acetate is fed to the reactor under the above temperature and LHSV conditions, acetic acid conversion may be at least 80%, e.g., at least 85% or at least 90%. The selectivity to ethyl acetate may be less than 20%, e.g., less than 15%, less than 10%, less than 0%, less than −5%, less than −15% or less than −20%. When selectivity to ethyl acetate is negative, this indicates that some ethyl acetate in the mixed feed stream is being converted.

In still other embodiments, the temperature in the reactor is at least 300° C. and the LHSV of the feed stream is at least 0.3 hr$^{-1}$. The LHSV may range from 0.3 hr$^{-1}$ to 1 hr$^{-1}$, e.g., from 0.3 hr$^{-1}$ to 0.8 hr$^{-1}$ or from 0.3 hr$^{-1}$ to 0.6 hr$^{-1}$. Under these conditions, when acetic acid is fed to the reactor, acetic acid conversion may be at least 85%, e.g., at least 87.5%, or at least 90%. The selectivity to ethyl acetate may be less than 25%, e.g., less than 22.5%, less than 20% or less than 17.5%. When a mixed feed stream comprising acetic acid and ethyl acetate is fed to the reactor under the above temperature and LHSV conditions, acetic acid conversion may be at least 85%, e.g., at least 87.5% or at least 90%. The selectivity to ethyl acetate may be less than 15%, e.g., less than 10%, less than 5%, less than 0%, less than −5%, less than −15% or less than −30%. When selectivity to ethyl acetate is negative, this indicates that some ethyl acetate in the mixed feed stream is being converted.

Acetic Acid Hydrogenation

As explained above, the invention is to a process for producing ethanol by hydrogenating a feed stream comprising compounds selected from acetic acid, ethyl acetate and mixtures thereof in the presence of any of the above-described catalysts. One particular preferred reaction is to make ethanol from acetic acid. The hydrogenation reaction may be represented as follows:

In some embodiments, the catalyst may be characterized as a bifunctional catalyst in that it effectively catalyzes the hydrogenation of acetic acid to ethanol as well as the conversion of ethyl acetate to one or more products, preferably ethanol.

The raw materials, acetic acid and hydrogen, fed to the reactor used in connection with the process of this invention may be derived from any suitable source including natural gas, petroleum, coal, biomass, and so forth. As examples, acetic acid may be produced via methanol carbonylation, acetaldehyde oxidation, ethane oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from other carbon sources have drawn increasing interest. In particular, when petroleum is relatively expensive, it may become advantageous to produce acetic acid from synthesis gas ("syngas") that is derived from other available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Biomass-derived syngas has a detectable $^{14}C$ isotope content as compared to fossil fuels such as coal or natural gas. An equilibrium forms in the Earth's atmosphere between constant new formation and constant degradation, and so the proportion of the $^{14}C$ nuclei in the carbon in the atmosphere on Earth is constant over long periods. The same distribution ratio $n^{14}C:n^{12}C$ ratio is established in living organisms as is present in the surrounding atmosphere, which stops at death and $^{14}C$ decomposes at a half life of about 6000 years. Methanol, acetic acid and/or ethanol formed from biomass-derived syngas would be expected to have a $^{14}C$ content that is substantially similar to living organisms. For example, the $^{14}C:^{12}C$ ratio of the methanol, acetic acid and/or ethanol may be from one half to about 1 of the $^{14}C:^{12}C$ ratio for living organisms. In other embodiments, the syngas, methanol, acetic acid and/or ethanol described herein are derived wholly from fossil fuels, i.e. carbon sources produced over 60,000 years ago, may have no detectable $^{14}C$ content.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally, in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. No. 6,509,180, and U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. Another biomass source is black liquor, which is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form syngas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into syngas, and U.S. Pat. No. 6,685,754, which discloses a method for the production of a hydrogen-containing gas composition, such as a syngas including hydrogen and carbon monoxide, are incorporated herein by reference in their entireties.

The acetic acid fed to the hydrogenation reactor may also comprise other carboxylic acids and anhydrides, as well as aldehyde and/or ketones, such as acetaldehyde and acetone. In one embodiment, the feed stream comprises acetic acid and ethyl acetate, which is referred to as a mixed stream. A mixed stream may comprise from 40 to 95 wt. % acetic acid and from 5 to 60 wt. % ethyl acetate. A suitable acetic acid feed stream comprises one or more of the compounds selected from the group consisting of acetic acid, acetic anhydride, acetaldehyde, ethyl acetate, diethyl acetal, diethyl ether, and mixtures thereof. These other compounds may also be hydrogenated in the processes of the present invention. In some embodiments, the presence of carboxylic acids, such as propanoic acid or its aldehyde, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the hydrogenation reactor without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

The reactor, in some embodiments, may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles. In some embodiments, multiple catalyst beds are employed in the same reactor or in different reactors, e.g., in series. For example, in one embodiment, a first catalyst functions in a first catalyst stage as a catalyst for the hydrogenation of a carboxylic acid, e.g., acetic acid, to its corresponding alcohol, e.g., ethanol, and a second bifunctional catalyst is employed in the second stage for converting unreacted acetic acid to ethanol as well as converting byproduct ester, e.g., ethyl acetate, to additional products, preferably to ethanol. The catalysts of the invention may be employed in either or both the first and/or second stages of such reaction systems.

The hydrogenation in the reactor may be carried out in either the liquid phase or vapor phase. Preferably, the reaction is carried out in the vapor phase under the following conditions. The reaction temperature may range from greater than 225° C. to 300° C., e.g., from 250° C. to 300° C., from 275° C. to 300° C. The pressure may range from 10 kPa to 3000 kPa, e.g., from 50 kPa to 2300 kPa, or from 100 kPa to 2000 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 18:1 to 2:1. Most preferably, the molar ratio of hydrogen to acetic acid is greater than 2:1, e.g., greater than 4:1 or greater than 8:1. For a mixed feed stream, the molar ratio of hydrogen to ethyl acetate may be greater than 5:1, e.g., greater than 10:1 or greater than 15:1.

Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

In various embodiments of the present invention, the crude ethanol product produced by the reactor, before any subsequent processing, such as purification and separation, will typically comprise unreacted acetic acid, ethanol and water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 40 | 5 to 30 | 10 to 30 | 10 to 26 |
| Ethyl Acetate | 0.1 to 40 | 0.1 to 25 | 0.1 to 20 | 0.1 to 15 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product may comprise acetic acid in an amount less than 20 wt. %, e.g., of less than 15 wt. %, less than 10 wt. % or less than 5 wt. %. In terms of ranges, the acetic acid concentration of Table 1 may range from 0.1 wt. % to 20 wt. %, e.g., 0.1 wt. % to 15 wt. %, from 0.1 wt. % to 10 wt. % or from 0.1 wt. % to 5 wt. %. In embodiments having lower amounts of acetic acid, the conversion of acetic acid is preferably greater than 75%, e.g., greater than 85% or greater than 90%. In addition, the selectivity to ethanol may also be preferably high, and is greater than 75%, e.g., greater than 85% or greater than 90%.

An ethanol product may be recovered from the crude ethanol product produced by the reactor using the catalyst of the present invention may be recovered using several different techniques.

The ethanol product may be an industrial grade ethanol comprising from 75 to 96 wt. % ethanol, e.g., from 80 to 96 wt. % or from 85 to 96 wt. % ethanol, based on the total weight of the ethanol product. The industrial grade ethanol may have a water concentration of less than 12 wt. % water, e.g., less than 8 wt. % or less than 3 wt. %. In some embodiments, when further water separation is used, the ethanol product preferably contains ethanol in an amount that is greater than 96 wt. %, e.g., greater than 98 wt. % or greater than 99.5 wt. %. The ethanol product having further water separation preferably comprises less than 3 wt. % water, e.g., less than 2 wt. % or less than 0.5 wt. %.

The finished ethanol composition produced by the embodiments of the present invention may be used in a variety of applications including fuels, solvents, chemical feedstocks, pharmaceutical products, cleansers, sanitizers, hydrogen transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, the finished ethanol composition may be esterified with acetic acid. In another application, the finished ethanol composition may be dehydrated to produce ethylene. Any known dehydration catalyst, such as zeolite catalysts or phosphotungstic acid catalysts, can be employed to dehydrate ethanol, as described in U.S. Pub. Nos. 2010/0030002 and 2010/0030001 and WO2010146332, the entire contents and disclosures of which are hereby incorporated by reference.

Catalyst Composition

The present invention also relates to the hydrogenation of acetic acid and/or ethyl acetate in the presence of a catalyst. The catalysts preferably comprise a precious metal and one or more active metals on a support, preferably a modified support, and may be suitable in catalyzing the hydrogenation of a carboxylic acid, e.g., acetic acid, and/or esters thereof, e.g., ethyl acetate, to the corresponding alcohol, e.g., ethanol.

In one embodiment, the catalyst comprises a precious metal and one or more active metals on a support. Preferably the support is a modified support comprising a support material and a support modifier comprising a metal selected from tungsten, molybdenum, vanadium, niobium and tantalum. In one aspect, the modified support comprises one or more of the active metals that are also disposed on the support, i.e., one or more of the active metals are part of the modified support and also disposed on top of the modified support.

It has now been discovered that such catalysts are particularly effective as multifunctional hydrogenation catalysts capable of converting both carboxylic acids, such as acetic acid, and esters thereof, e.g., ethyl acetate, to their corresponding alcohol(s), e.g., ethanol, under hydrogenation conditions. Thus, in another embodiment, the inventive catalyst comprises a precious metal and an active metal on a modified support, wherein the catalyst is effective for providing an acetic acid conversion greater than 20%, greater than 75% or greater than 90%, and an ethyl acetate conversion greater than 0%, greater than 10% or greater than 20%.

Precious and Active Metals

The catalysts of the invention preferably include at least one precious metal impregnated on the catalyst support. The precious metal may be selected, for example, from rhodium, rhenium, ruthenium, platinum, palladium, osmium, iridium and gold. Preferred precious metals for the catalysts of the invention include palladium, platinum, and rhodium. The precious metal preferably is catalytically active in the hydrogenation of a carboxylic acid and/or its ester to the corresponding alcohol(s). The precious metal may be in elemental form or in molecular form, e.g., an oxide of the precious metal. The catalyst comprises such precious metals in an amount less than 5 wt. %, e.g., less than 3 wt. %, less than 2 wt. %, less than 1 wt. % or less than 0.5 wt. %. In terms of ranges, the catalyst may comprise the precious metal in an amount from 0.05 to 10 wt. %, e.g. from 0.1 to 5 wt. %, or from 0.1 to 3 wt. %, based on the total weight of the catalyst. In some embodiments, the metal loading of the precious metal may be less than the metal loadings of the one or more active metals.

In addition to the precious metal, the catalyst includes one or more active metals disposed on the modified support. In one embodiment, the modified support also comprises one or more active metals, such as cobalt and tin. Without being bound by theory, the active metals when part of the modified support may disperse the support modifier metal or oxide thereof on the support. An active metal is part of the modified support when it is impregnated and calcined on the support prior to the impregnation or introduction of the precious metal to the modified support. The same active metals may be part of the modified support and disposed on the support modifier. In particular, it may be preferred to use cobalt and tin.

As used herein, active metals refer to catalytically active metals that improve the conversion, selectivity and/or productivity of the catalyst and may include precious or non-precious active metals. Thus, a catalyst comprising a precious metal and an active metal may include: (i) one (or more) precious metals and one (or more) non-precious active metals, or (ii) may comprise two (or more) precious metals. Thus, precious metals are included herein as exemplary active metals. Further, it should be understood that use of the term "active metal" to refer to some metals in the catalysts of the invention is not meant to suggest that the precious metal that is also included in the inventive catalysts is not catalytically active.

In one embodiment, the one or more active metals included in the catalyst are selected from the group consisting of copper, iron, cobalt, vanadium, nickel, titanium, zinc, chromium, molybdenum, tungsten, tin, lanthanum, cerium, manganese, any of the aforementioned precious metals, in particular rhenium, ruthenium, and gold, and combinations thereof. Preferably, however, the one or more active metals do not include any precious metals, and thus include copper, iron, cobalt, vanadium, nickel, titanium, zinc, chromium, molybdenum, tungsten, tin, lanthanum, cerium, manganese, and combinations thereof. More preferably, the one or more active metals are selected from the group consisting of copper, iron, cobalt, nickel, chromium, molybdenum, tungsten and tin, and more preferably the one or more active metals are selected from cobalt, tin and tungsten. In one embodiment, the active metal may comprise tin in combination with at least one other active metal. The one or more active metals may be in elemental form or in molecular form, e.g., an oxide of the active metal, or a combination thereof.

The total weight of all the active metals, including the aforementioned precious metal, present in the catalyst preferably is from 0.1 to 25 wt. %, e.g., from 0.5 to 15 wt. %, or from 1.0 to 10 wt. %. In one embodiment, the catalyst may comprise from cobalt in an amount from 0.5 to 20 wt. %, e.g., preferably from 4.1 to 20 wt. %, and tin in an amount from 0.5 to 20 wt. %, e.g., preferably from 0.5 to 3.5 wt. %. The active metals for purposes of the present invention may be disposed on the modified support and may be part of the modified support. The total weight of the active metal may include the combined weight of the metal in the modified support and the metal disposed on the modified support. Thus, for example, the modified support may comprise from 0.1 to 15 wt. %, e.g. from 0.5 to 10 wt. %, of the one or more active metals and the one or more active metals disposed on the modified support may be present in an amount from 0.1 to 15 wt. %, e.g., from 0.5 to 10 wt. %, provided that the total metal loading of the one or more active metals is less than 25 wt. %. For purposes of the present specification, unless otherwise indicated, weight percent is based on the total weight the catalyst including metal and support.

In some embodiments, the catalyst contains at least two active metals in addition to the precious metal. The at least two active metals may be selected from any of the active metals identified above, so long as they are not the same as the precious metal or each other. Additional active metals may also be used in some embodiments. Thus, in some embodiments, there may be multiple active metals on the support in addition to the precious metal.

Preferred bimetallic (precious metal+active metal) combinations for some exemplary catalyst compositions include platinum/tin, platinum/ruthenium, platinum/rhenium, platinum/cobalt, platinum/nickel, palladium/ruthenium, palladium/rhenium, palladium/cobalt, palladium/copper, palladium/nickel, ruthenium/cobalt, gold/palladium, ruthenium/rhenium, ruthenium/iron, rhodium/iron, rhodium/cobalt, rhodium/nickel and rhodium/tin. In some embodiments, the catalyst comprises three metals on a support, e.g., one precious metal and two active metals. Exemplary tertiary combinations may include palladium/rhenium/tin, palladium/rhenium/cobalt, palladium/rhenium/nickel, palladium/cobalt/tin, platinum/tin/palladium, platinum/tin/rhodium, platinum/tin/gold, platinum/tin/iridium, platinum/cobalt/tin, platinum/tin/copper, platinum/tin/chromium, platinum/tin/zinc, platinum/tin/nickel, rhodium/nickel/tin, rhodium/cobalt/tin and rhodium/iron/tin. In one preferred embodiment, the tertiary combination comprises cobalt or tin or both cobalt and tin. In some embodiments, the catalyst may comprise more than three metals on the support.

When the catalyst comprises a precious metal and one active metal on a support, the active metal is present in an amount from 0.1 to 20 wt. %, e.g., from 0.1 to 10 wt. %, or from 0.1 to 7.5 wt. %. When the catalyst comprises two or more active metals in addition to the precious metal, e.g., a first active metal and a second active metal, the first active metal may be present in the catalyst in an amount from 0.05 to 20 wt. %, e.g. from 0.1 to 10 wt. %, or from 0.5 to 5 wt. %. The second active metal may be present in an amount from 0.05 to 20 wt. %, e.g., from 0.1 to 10 wt. %, or from 0.5 to 7.5 wt. %. If the catalyst further comprises a third active metal, the third active metal may be present in an amount from 0.05 to 20 wt. %, e.g., from 0.05 to 10 wt. %, or from 0.05 to 7.5 wt. %. When the second or third active metal is cobalt, in one embodiment, the metal loading may be from 4.1 to 20 wt. %, e.g., from 4.1 to 10 wt. % or from 4.1 to 7.5 wt. %. The active metals may be alloyed with one another or may comprise a non-alloyed metal solution, a metal mixture or be present as one or more metal oxides.

The preferred metal ratios may vary somewhat depending on the active metals used in the catalyst. In some embodiments, the mole ratio of the precious metal to the one or more active metals is from 10:1 to 1:10, e.g., from 4:1 to 1:4, from 2:1 to 1:2 or from 1.5:1 to 1:1.5. In another embodiment, the precious metal may be present in an amount from 0.1 to 5 wt. %, the first active metal in an amount from 0.5 to 20 wt. % and the second active metal in an amount from 0.5 to 20 wt. %, based on the total weight of the catalyst. In another embodiment, the precious metal is present in an amount from 0.1 to 5 wt. %, the first active metal in an amount from 0.5 to 15 wt. % and the second active metal in an amount from 0.5 to 15 wt. %.

In one embodiment, the first and second active metals are present as cobalt and tin, and, when added to the catalyst together and calcined together, are present at a cobalt to tin molar ratio from 6:1 to 1:6 or from 3:1 to 1:3. The cobalt and tin may be present in substantially equimolar amounts, when added to the catalyst together and calcination together. In another embodiment, when cobalt is added to the support material initially and calcined as part of the modified support and tin is subsequently added to the modified support, it is preferred to have a cobalt to tin molar that is greater than 4:1, e.g., greater than 6:1 or greater than 11:1. Without being bound by theory the excess cobalt, based on molar amount relative to tin, may improve the multifunctionality of the catalyst.

Support Materials

The catalysts of the present invention comprise a suitable support material, preferably a modified support material. In one embodiment, the support material may be an inorganic oxide. In one embodiment, the support material may be selected from the group consisting of silica, alumina, titania, silica/alumina, pyrogenic silica, high purity silica, zirconia, carbon (e.g., carbon black or activated carbon), zeolites and mixtures thereof. Preferably, the support material comprises a silicaceous support material such as silica, pyrogenic silica, or high purity silica. In one embodiment the silicaceous support material is substantially free of alkaline earth metals, such as magnesium and calcium. In preferred embodiments, the support material is present in an amount from 25 wt. % to 99 wt. %, e.g., from 30 wt. % to 98 wt. % or from 35 wt. % to 95 wt. %, based on the total weight of the catalyst.

In preferred embodiments, the support material comprises a silicaceous support material, e.g., silica, having a surface area of at least 50 $m^2/g$, e.g., at least 100 $m^2/g$, or at least 150 $m^2/g$. In terms of ranges, the silicaceous support material preferably has a surface area from 50 to 600 $m^2/g$, e.g., from 100 to 500 $m^2/g$ or from 100 to 300 $m^2/g$. High surface area silica, as used throughout the application, refers to silica having a surface area of at least 250 $m^2/g$. For purposes of the present specification, surface area refers to BET nitrogen surface area, meaning the surface area as determined by ASTM D6556-04, the entirety of which is incorporated herein by reference.

The preferred silicaceous support material also preferably has an average pore diameter from 5 to 100 nm, e.g., from 5 to 30 nm, from 5 to 25 nm or from 5 to 10 nm, as determined by mercury intrusion porosimetry, and an average pore volume from 0.5 to 2.0 $cm^3/g$, e.g., from 0.7 to 1.5 $cm^3/g$ or from 0.8 to 1.3 $cm^3/g$, as determined by mercury intrusion porosimetry.

The morphology of the support material, and hence of the resulting catalyst composition, may vary widely. In some exemplary embodiments, the morphology of the support material and/or of the catalyst composition may be pellets, extrudates, spheres, spray dried microspheres, rings, pentarings, trilobes, quadrilobes, multi-lobal shapes, or flakes although cylindrical pellets are preferred. Preferably, the silicaceous support material has a morphology that allows for a packing density from 0.1 to 1.0 $g/cm^3$, e.g., from 0.2 to 0.9 $g/cm^3$ or from 0.3 to 0.8 $g/cm^3$. In terms of size, the silica support material preferably has an average particle size, meaning the average diameter for spherical particles or average longest dimension for non-spherical particles, from 0.01 to 1.0 cm, e.g., from 0.1 to 0.7 cm or from 0.2 to 0.5 cm. Since the precious metal and the one or more active metals that are disposed on the support are generally in the form of very small metal (or metal oxide) particles or crystallites relative to the size of the support, these metals should not substantially impact the size of the overall catalyst particles. Thus, the above particle sizes generally apply to both the size of the support as well as to the final catalyst particles, although the catalyst particles are preferably processed to form much larger catalyst particles, e.g., extruded to form catalyst pellets.

Support Modifiers

The support material preferably comprises a support modifier. A support modifier may adjust the acidity of the support material. In one embodiment, a support modifier comprises a metal selected from the group consisting of tungsten, molybdenum, vanadium, niobium, and tantalum. The metal for the support modifier may be an oxide thereof. In one embodiment, the support modifiers are present in an amount from 0.1 wt. % to 50 wt. %, e.g., from 0.2 wt. % to 25 wt. %, from 0.5 wt. % to 20 wt. %, or from 1 wt. % to 15 wt. %, based on the total weight of the catalyst. When the support modifier comprises tungsten, molybdenum, and vanadium, the support modifier may be present in an amount from 0.1 to 40 wt. %, e.g., from 0.1 to 30 wt. % or from 0.1 to 20 wt. %, based on the total weight of the catalyst.

As indicated, the support modifiers may adjust the acidity of the support. For example, the acid sites, e.g., Brønsted acid sites or Lewis acid sites, on the support material may be adjusted by the support modifier to favor selectivity to ethanol during the hydrogenation of acetic acid and/or esters thereof. The acidity of the support material may be adjusted by optimizing surface acidity of the support material. The support material may also be adjusted by having the support modifier change the pKa of the support material. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference. In general, the surface acidity of the support may be adjusted based on the composition of the feed stream being sent to the hydrogenation process in order to maximize alcohol production, e.g., ethanol production.

In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIII metals, aluminum oxides, and mixtures thereof. In one embodiment, the support modifier comprises metal selected from the group consisting of tungsten, molybdenum, vanadium, niobium, and tantalum.

In one embodiment, the acidic modifier may also include those selected from the group consisting of $WO_3$, $MoO_3$, $V_2O_5$, $VO_2$, $V_2O_3$, $Nb_2O_5$, $Ta_2O_5$, FeO, $Fe_3O_4$, $Fe_2O_3$, $Cr_2O_3$, $MnO_2$, CoO, $Co_2O_3$, and $Bi_2O_3$. Reduced tungsten oxides or molybdenum oxides may also be employed, such as, for example, one or more of $W_{20}O_{58}$, $WO_2$, $W_{49}O_{119}$, $W_{50}O_{148}$, $W_{18}O_{49}$, $Mo_9O_{26}$, $Mo_8O_{23}$, $Mo_5O_{14}$, $Mo_{17}O_{47}$, $Mo_4O_{11}$, or $MoO_2$. In one embodiment, the tungsten oxide may be cubic tungsten oxide ($H_{0.5}WO_3$). It has now surprisingly and unexpectedly been discovered that the use of such metal oxide support modifiers in combination with a precious metal and one or more active metals may result in catalysts having multifunctionality, and which may be suitable for converting a carboxylic acid, such as acetic acid, as well as corresponding esters thereof, e.g., ethyl acetate, to one or more hydrogenation products, such as ethanol, under hydrogenation conditions.

In other embodiments, the acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Acidic support modifiers include those selected from the group consisting of $TiO_2$, $ZrO_2$, $Nb_2O_5$, $Ta_2O_5$, and $Al_2O_3$.

In some embodiments, the acidic support modifier comprises a mixed metal oxide comprising at least one of the active metals and an oxide anion of a Group IVB, VB, VIB, VIII metal, such as tungsten, molybdenum, vanadium, niobium or tantalum. The oxide anion, for example, may be in the form of a tungstate, molybdate, vanadate, or niobate. Exemplary mixed metal oxides include cobalt tungstate, copper tungstate, iron tungstate, zirconium tungstate, manganese tungstate, cobalt molybdate, copper molybdate, iron molybdate, zirconium molybdate, manganese molybdate, cobalt vanadate, copper vanadate, iron vanadate, zirconium vanadate, manganese vanadate, cobalt niobate, copper niobate, iron niobate, zirconium niobate, manganese niobate, cobalt tantalate, copper tantalate, iron tantalate, zirconium tantalate, and/or manganese tantalate. In one embodiment, the catalyst does not comprise and is substantially free of tin tungstate. It has now been discovered that catalysts containing such mixed metal support modifiers may provide the desired degree of multifunctionality at increased conversion, e.g., increased ester conversion, and with reduced byproduct formation, e.g., reduced diethyl ether formation.

In one embodiment, the catalyst comprises from 0.25 to 1.25 wt. % platinum, from 1 to 10 wt. % cobalt, and from 1 to 10 wt. % tin on a silica or a silica-alumina support material.

The cobalt and tin may be disposed on the support material and may be part of the modified support. The support material may comprise from 5 to 15 wt. % acidic support modifiers, such as $WO_3$, $V_2O_5$ and/or $MoO_3$. In one embodiment, the acidic modifier may comprise cobalt tungstate, e.g., in an amount from 0.1 to 20 wt. %, or from 5 to 15 wt. %.

In some embodiments, the modified support comprises one or more active metals in addition to one or more acidic modifiers. The modified support may, for example, comprise one or more active metals selected from copper, iron, cobalt, vanadium, nickel, titanium, zinc, chromium, molybdenum, tungsten, tin, lanthanum, cerium, and manganese. For example, the support may comprise an active metal, preferably not a precious metal, and an acidic or basic support modifier. Preferably, the support modifier comprises a support modifier metal selected from the group consisting of tungsten, molybdenum, vanadium, niobium, and tantalum. In this aspect, the final catalyst composition comprises a precious metal, and one or more active metals disposed on the modified support. In a preferred embodiment, at least one of the active metals in the modified support is the same as at least one of the active metals disposed on the support. For example, the catalyst may comprise a support modified with cobalt, tin and tungsten (optionally as $WO_3$, $H_{0.5}WO_3$, $HWO_4$, and/or as cobalt tungstate). In this example, the catalyst further comprises a precious metal, e.g., palladium, platinum or rhodium, and at least one active metal, e.g., cobalt and/or tin, disposed on the modified support. In another embodiment, the catalyst may comprise a support modified with tungsten. In yet another example, the catalyst may comprise a support modified with tungsten and cobalt.

Without being by bound theory, it is believed that the presence of tin tungstate on the modified support or catalyst tends to decrease catalytic activity in the conversion of acetic acid to ethanol. When used on the modified support, tin does contribute to improved catalytic activity and catalyst lifetime. However, when tin is present with tungsten, the undesirable tin tungstate species may form. To prevent the formation of tin tungstate, it has been found the use of cobalt may inhibit the formation of tin tungstate. This allows the preferential formation of cobalt tungstate over tin tungstate. In addition, this allows the use of tin on the modified support to thus maintain sufficient catalyst activity and catalyst lifetime. In one embodiment, the modified support comprises cobalt tungstate and tin, but the modified support is substantially free of tin tungstate.

Processes for Making the Catalyst

The present invention also relates to processes for making the catalyst. Without being bound by theory, the process for making the catalyst may improve one or more of acetic acid conversion, ester conversion, ethanol selectivity and overall productivity. In one embodiment, the support is modified with one or more support modifiers and the resulting modified support is subsequently impregnated with a precious metal and one or more active metals to form the catalyst composition. For example, the support may be impregnated with a support modifier solution comprising a support modifier precursor and optionally one or more active metal precursors to form the modified support. After drying and calcination, the resulting modified support is impregnated with a second solution comprising precious metal precursor and optionally one or more of the active metal precursors, followed by drying and calcination to form the final catalyst.

In this embodiment, the support modifier solution may comprise a support modifier metal precursor and one or more active metal precursors, more preferably at least two active metal precursors. The precursors preferably are comprised of salts of the respective metals in solution, which, when heated, are converted to elemental metallic form or to a metal oxide. Since, in this embodiment, two or more active metal precursors are impregnated onto the support material simultaneously and/or sequentially with the support modifier precursor, one or more of the resulting active metals may interact with the support modifier metal at a molecular metal upon formation to form one or more polymetallic crystalline species, such as cobalt tungstate. In other embodiments, one or more of the active metals will not interact with the support modifier metal precursor and are separately deposited on the support material, e.g., as discrete metal nanoparticles or as an amorphous metal mixture. Thus, the support material may be modified with one or more active metal precursors at the same time that it is modified with a support modifier metal, and the resulting active metals may or may not interact with the support modifier metal to form one or more polymetallic crystalline species.

In some embodiments, the support modifier may be added as particles to the support material. For example, one or more support modifier precursors, if desired, may be added to the support material by mixing the support modifier particles with the support material, preferably in water. When mixed it is preferred for some support modifiers to use a powdered material of the support modifiers. If a powdered material is employed, the support modifier may be pelletized, crushed and sieved prior to being added to the support.

As indicated, in most embodiments, the support modifier preferably is added through a wet impregnation step. Preferably, a support modifier precursor to the support modifier may be used. Some exemplary support modifier precursors include alkali metal oxides, alkaline earth metal oxides, Group IIB metal oxides, Group IIIB metal oxides, Group IVB metal oxides, Group VB metal oxides, Group VIB metal oxides, Group VIIB metal oxides, and/or Group VIII metal oxides, as well as preferably aqueous salts thereof.

Although the overwhelming majority of metal oxides and polyoxoion salts are insoluble, or have a poorly defined or limited solution chemistry, the class of isopoly- and heteropolyoxoanions of the early transition elements forms an important exception. These complexes may be represented by the general formulae:

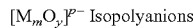
[$M_mO_y$]$^{p-}$ Isopolyanions

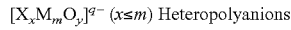
[$X_xM_mO_y$]$^{q-}$ ($x \leq m$) Heteropolyanions where M is selected from tungsten, molybdenum, vanadium, niobium, tantalum and mixtures thereof, in their highest ($d^0$, $d^1$) oxidations states. Such polyoxometalate anions form a structurally distinct class of complexes based predominately, although not exclusively, upon quasi-octahedrally-coordinated metal atoms. The elements that can function as the addenda atoms, M, in heteropoly- or isopolyanions may be limited to those with both a favorable combination of ionic radius and charge and the ability to form $d_\pi$-$p_\pi$ M—O bonds. There is little restriction, however, on the heteroatom, X, which may be selected from virtually any element other than the rare gases. See, e.g., M. T. Pope, *Heteropoly and Isopoly Oxometalates*, Springer Verlag, Berlin, 1983, 180; Chapt. 38, *Comprehensive Coordination Chemistry*, Vol. 3, 1028-58, Pergamon Press, Oxford, 1987, the entireties of which are incorporated herein by reference.

Polyoxometalates (POMs) and their corresponding heteropoly acids (HPAs) have several advantages making them economically and environmentally attractive. First, HPAs have a very strong approaching the superacid region, Bronsted acidity. In addition, they are efficient oxidants exhibiting fast reversible multielectron redox transformations under rather mild conditions. Solid HPAs also possess a discrete ionic structure, comprising fairly mobile basic structural units, e.g., heteropolyanions and countercations ($H^+$, $H_3O^+$, $H_5O_2^+$, etc.), unlike zeolites and metal oxides.

In view of the foregoing, in some embodiments, the support modifier precursor comprises a POM, which preferably comprises a metal selected from the group consisting of tungsten, molybdenum, niobium, vanadium and tantalum. In some embodiments, the POM comprises a hetero-POM. A non-limiting list of suitable POMs includes phosphotungstic acid (H—$PW_{12}$)($H_3PW_{12}O_{40}$·$nH_2O$), ammonium metatungstate (AMT) (($NH_4$)$_6H_2W_{12}O_{40}$·$H_2O$), ammonium heptamolybdate tetrahydrate, (AHM) (($NH_4$)$_6Mo_7O_{24}$·$4H_2O$), silicotungstic acid hydrate (H—$SiW_{12}$)($H_4SiW_{12}O_{40}$·$H_2O$), silicomolybdic acid (H—$SiMo_{12}$)($H_4SiMo_{12}O_{40}$·$nH_2O$), and phosphomolybdic acid (H—$PMo_{12}$)($H_3PMo_{12}O_{40}$·$nH_2O$).

The use of POM-derived support modifiers in the catalyst compositions of the invention has now surprising and unexpectedly been shown to provide bi- or multi-functional catalyst functionality, desirably resulting in conversions for both acetic acid and byproduct esters such as ethyl acetate, thereby rendering them suitable for catalyzing mixed feeds comprising, for example, acetic acid and ethyl acetate.

Impregnation of the precious metal and one or more active metals onto the support, e.g., modified support, may occur simultaneously (co-impregnation) or sequentially. In simultaneous impregnation, the two or more metal precursors are mixed together and added to the support, preferably modified support, together followed by drying and calcination to form the final catalyst composition. With simultaneous impregnation, it may be desired to employ a dispersion agent, surfactant, or solubilizing agent, e.g., ammonium oxalate or an acid such as acetic or nitric acid, to facilitate the dispersing or solubilizing of the first, second and/or optional third metal precursors in the event the two precursors are incompatible with the desired solvent, e.g., water.

In sequential impregnation, the first metal precursor may be first added to the support followed by drying and calcining, and the resulting material may then be impregnated with the second metal precursor followed by an additional drying step followed by a calcining step to form the final catalyst composition. Additional metal precursors (e.g., a third metal precursor) may be added either with the first and/or second metal precursor or in a separate third impregnation step, followed by drying and calcination. Of course, combinations of sequential and simultaneous impregnation may be employed if desired.

In embodiments where the precious metal and/or one or more active metals, e.g., one or more of the first, second or third metals, are applied to the catalyst sequentially, i.e., in multiple impregnation steps, the catalyst may be said to comprise a plurality of "theoretical layers." For example, where a first metal is impregnated onto a support followed by impregnation of a second metal, the resulting catalyst may be said to have a first theoretical layer comprising the first metal and a second theoretical layer comprising the second metal. As discussed above, in some aspects, more than one active metal precursor may be co-impregnated onto the support in a single step such that a theoretical layer may comprise more than one metal or metal oxide. In another aspect, the same metal precursor may be impregnated in multiple sequential impregnation steps leading to the formation of multiple theoretical layers containing the same metal or metal oxide. In this context, notwithstanding the use of the term "layers," it will be appreciated by those skilled in the art that multiple layers may or may not be formed on the catalyst support depending, for example, on the conditions employed in catalyst formation, on the amount of metal used in each step and on the specific metals employed.

The use of a solvent, such as water, glacial acetic acid, a strong acid such as hydrochloric acid, nitric acid, or sulfuric acid, or an organic solvent, is preferred in the support modification step, e.g., for impregnating a support modifier precursor onto the support material. The support modifier solution comprises the solvent, preferably water, a support modifier precursor, and preferably one or more active metal precursors. The solution is stirred and combined with the support material using, for example, incipient wetness techniques in which the support modifier precursor is added to a support material having the same pore volume as the volume of the solution. Impregnation occurs by adding, optionally drop wise, a solution containing the precursors of either or both the support modifiers and/or active metals, to the dry support material. Capillary action then draws the support modifier into the pores of the support material. The thereby impregnated support can then be formed by drying, optionally under vacuum, to drive off solvents and any volatile components within the support mixture and depositing the support modifier on and/or within the support material. Drying may occur, for example, at a temperature from 50° C. to 300° C., e.g., from 100° C. to 200° C. or about 120° C., optionally for a period from 1 to 24 hours, e.g., from 3 to 15 hours or from 6 to 12 hours. The dried support may be calcined optionally with ramped heating, for example, at a temperature from 300° C. to 900° C., e.g., from 400° C. to 750° C., from 500° C. to 600° C. or at about 550° C., optionally for a period of time from 1 to 12 hours, e.g., from 2 to 10 hours, from 4 to 8 hours or about 6 hours, to form the final modified support. Upon heating and/or the application of vacuum, the metal(s) of the precursor(s) preferably decompose into their oxide or elemental form. In some cases, the completion of removal of the solvent may not take place until the catalyst is placed into use and/or calcined, e.g., subjected to the high temperatures encountered during operation. During the calcination step, or at least during the initial phase of use of the catalyst, such compounds are converted into a catalytically active form of the metal or a catalytically active oxide thereof.

Once formed, the modified supports may be shaped into particles having the desired size distribution, e.g., to form particles having an average particle size in the range from 0.2 to 0.4 cm. The supports may be extruded, pelletized, tabletized, pressed, crushed or sieved to the desired size distribution. Any of the known methods to shape the support materials into desired size distribution can be employed. Alternatively, support pellets may be used as the starting material used to make the modified support and, ultimately, the final catalyst.

In one embodiment, the catalyst of the present invention may be prepared using a bulk catalyst technique. Bulk catalysts may be formed by precipitating precursors to support modifiers and one or more active metals. The precipitating may be controlled by changing the temperature, pressure, and/or pH. In some embodiments, the bulk catalyst preparation may use a binder. A support material may not be used in a bulk catalyst process. Once precipitated, the bulk catalyst may be shaped by spraying drying, pelleting, granulating, tablet pressing, beading, or pilling. Suitable bulk catalyst techniques may be used such as those described in Krijn P. de Jong, ed., Synthesis of Solid Catalysts, Wiley, (2009), pg. 308, the entire contents and disclosure of which is incorporated by reference.

In one embodiment, the precious metal and one or more active metals are impregnated onto the support, preferably onto any of the above-described modified supports. A precursor of the precious metal preferably is used in the metal impregnation step, such as a water soluble compound or water dispersible compound/complex that includes the precious metal of interest. Similarly, precursors to one or more active metals may also be impregnated into the support, preferably modified support. Depending on the metal precursors employed, the use of a solvent, such as water, glacial acetic acid, nitric acid or an organic solvent, may be preferred to help solubilize one or more of the metal precursors.

In one embodiment, separate solutions of the metal precursors are formed, which are subsequently blended prior to being impregnated on the support. For example, a first solution may be formed comprising a first metal precursor, and a second solution may be formed comprising the second metal precursor and optionally the third metal precursor. At least one of the first, second and optional third metal precursors preferably is a precious metal precursor, and the other(s) are preferably active metal precursors (which may or may not comprise precious metal precursors). Either or both solutions preferably comprise a solvent, such as water, glacial acetic acid, hydrochloric acid, nitric acid or an organic solvent.

In one exemplary embodiment, a first solution comprising a first metal halide is prepared. The first metal halide optionally comprises a tin halide, e.g., a tin chloride such as tin (II) chloride and/or tin (IV) chloride. Optionally, a second metal precursor, as a solid or as a separate solution, is combined with the first solution to form a combined solution. The second metal precursor, if used, preferably comprises a second metal oxalate, acetate, halide or nitrate, e.g., cobalt nitrate. The first metal precursor optionally comprises an active metal, optionally copper, iron, cobalt, nickel, chromium, molybdenum, tungsten, or tin, and the second metal precursor, if present, optionally comprises another active metal (also optionally copper, iron, cobalt, nickel, chromium, molybdenum, tungsten, or tin). A second solution is also prepared comprising a precious metal precursor, in this embodiment preferably a precious metal halide, such as a halide of rhodium, rhenium, ruthenium, platinum or palladium. The second solution is combined with the first solution or the combined solution, depending on whether the second metal precursor is desired, to form a mixed metal precursor solution. The resulting mixed metal precursor solution may then be added to the support, optionally a modified support, followed by drying and calcining to form the final catalyst composition as described above. The resulting catalyst may or may not be washed after the final calcination step. Due to the difficulty in solubilizing some precursors, it may be desired to reduce the pH of the first and/or second solutions, for example by employing an acid such as acetic acid, hydrochloric acid or nitric acid, e.g., 6 to 10 M $HNO_3$.

In another aspect, a first solution comprising a first metal oxalate is prepared, such as an oxalate of copper, iron, cobalt, nickel, chromium, molybdenum, tungsten, or tin. In this embodiment, the first solution preferably further comprises an acid such as acetic acid, hydrochloric acid, phosphoric acid or nitric acid, e.g., 6 to 10 M $HNO_3$. Optionally, a second metal precursor, as a solid or as a separate solution, is combined with the first solution to form a combined solution. The second metal precursor, if used, preferably comprises a second metal oxalate, acetate, halide or nitrate, and preferably comprises an active metal, also optionally copper, iron, cobalt, nickel, chromium, molybdenum, tungsten, or tin. A second solution is also formed comprising a precious metal oxalate, for example, an oxalate of rhodium, rhenium, ruthenium, platinum or palladium, and optionally further comprises an acid such as acetic acid, hydrochloric acid, phosphoric acid or nitric acid, e.g., 6 to 10 M $HNO_3$. The second solution is combined with the first solution or the combined solution, depending on whether the second metal precursor is desired, to form a mixed metal precursor solution. The resulting mixed metal precursor solution may then be added to the support, optionally a modified support, followed by drying and calcining to form the final catalyst composition as described above. The resulting catalyst may or may not be washed after the final calcination step.

In one embodiment, the impregnated support, optionally impregnated modified support, is dried at a temperature from 100° C. to 140° C., from 110° C. to 130° C., or about 120° C., optionally from 1 to 12 hours, e.g., from 2 to 10 hours, from 4 to 8 hours or about 6 hours. If calcination is desired, it is preferred that the calcination temperature employed in this step is less than the calcination temperature employed in the formation of the modified support, discussed above. The second calcination step, for example, may be conducted at a temperature that is at least 50° C., at least 100° C., at least 150° C. or at least 200° C. less than the first calcination step, i.e., the calcination step used to form the modified support. For example, the impregnated catalyst may be calcined at a temperature from 200° C. to 500° C., from 300° C. to 400° C., or about 350° C., optionally for a period from 1 to 12 hours, e.g., from 2 to 10 hours, from 4 to 8 hours or about 6 hours.

In one embodiment, ammonium oxalate is used to facilitate solubilizing of at least one of the metal precursors, e.g., a tin precursor, as described in U.S. Pat. No. 8,211,821, the entirety of which is incorporated herein by reference. In this aspect, the first metal precursor optionally comprises an oxalate of a precious metal, e.g., rhodium, palladium, or platinum, and a second metal precursor optionally comprises an oxalate tin. Another active metal precursor, if desired, comprises a nitrate, halide, acetate or oxalate of chromium, copper, or cobalt. In this aspect, a solution of the second metal precursor may be made in the presence of ammonium oxalate as solubilizing agent, and the first metal precursor may be added thereto, optionally as a solid or a separate solution. If used, the third metal precursor may be combined with the solution comprising the first precursor and tin oxalate precursor, or may be combined with the second metal precursor, optionally as a solid or a separate solution, prior to addition of the first metal precursor. In other embodiments, an acid such as acetic acid, hydrochloric acid or nitric acid may be substituted for the ammonium oxalate to facilitate solubilizing of the tin oxalate. The resulting mixed metal precursor solution may then be added to the support, optionally a modified support, followed by drying and calcining to form the final catalyst composition as described above.

The specific precursors used in the various embodiments of the invention may vary widely. Suitable metal precursors may include, for example, metal halides, amine solubilized metal hydroxides, metal nitrates or metal oxalates. For example, suitable compounds for platinum precursors and palladium precursors include chloroplatinic acid, ammonium chloroplatinate, amine solubilized platinum hydroxide, platinum nitrate, platinum tetra ammonium nitrate, platinum chloride, platinum oxalate, palladium nitrate, palladium tetra ammonium nitrate, palladium chloride, palladium oxalate, sodium palladium chloride, sodium platinum chloride, and platinum ammonium nitrate, $Pt(NH_3)_4(NO_4)_2$. Generally, both from the point of view of economics and environmental aspects, aqueous solutions of soluble compounds of platinum and palladium are preferred. In one embodiment, the precious metal precursor is not a metal halide and is substantially free of metal halides, while in other embodiments, as described above, the precious metal precursor is a halide.

In another example, the second and third metals are co-impregnated with the precursor to $WO_3$ on the support, optionally forming a mixed oxide with $WO_3$, e.g., cobalt tungstate, followed by drying and calcination. The resulting modified support may be impregnated, preferably in a single impregnation step or multiple impregnation steps, with one or more of the first, second and third metals, followed by a second drying and calcination step. In this manner, cobalt tungstate may be formed on the modified support. Again, the temperature of the second calcining step preferably is less than the temperature of the first calcining step.

The following examples describe the catalyst and process of this invention.

EXAMPLES

Comparative Example A and Examples 1-3

Figure 2:
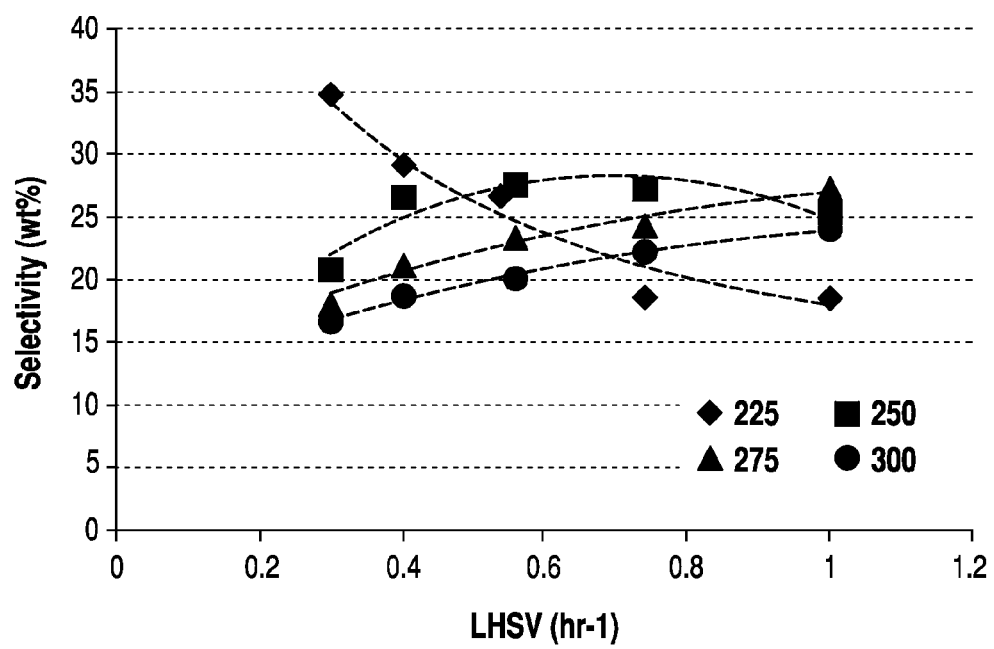
FIG. 2 shows ethyl acetate selectivity for one embodiment of the present invention.

A feed stream comprising acetic acid was fed to a Berty reactor in the presence of a hydrogenation catalyst comprising 1.06 wt. % platinum, 3.75 wt. % cobalt and 3.25 wt. % tin on a modified silica support comprising 3.75 wt. % cobalt, 3.25 wt. % tin, and 12 wt. % tungsten. Comparative Example A was fed to the reactor at a temperature of 225° C. Example 1 was fed to the reactor at a temperature of 250° C. Example 2 was fed to the reactor at a temperature of 275° C. Example 3 was fed to the reactor at a temperature of 300° C. The acetic acid conversion of each example is shown in FIG. 1. Selectivity of acetic acid to ethyl acetate for Comparative Example A and Examples 1-3 is shown in FIG. 2.

Comparative Example B and Examples 4-6

Figure 3:
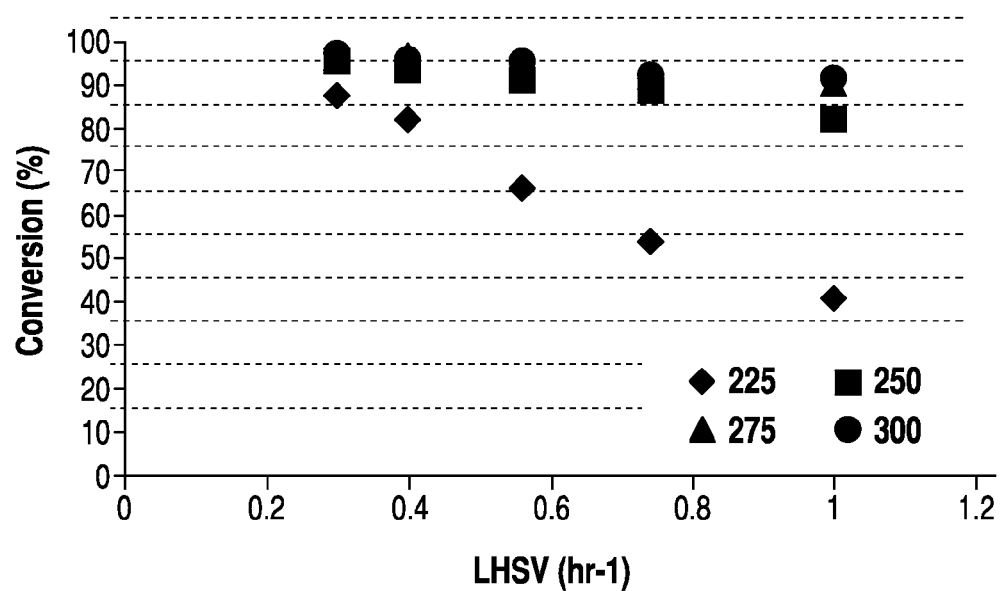
FIG. 3 shows feed stream conversion for another embodiment of the present invention.
Figure 4:
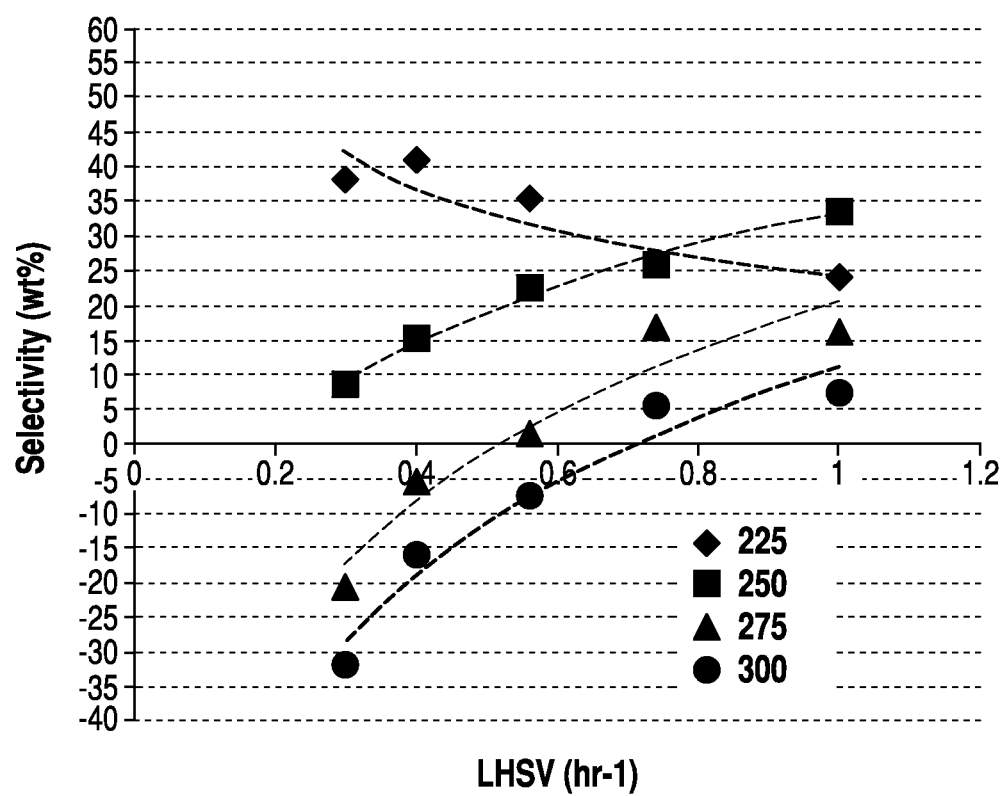
FIG. 4 shows ethyl acetate selectivity for another embodiment of the present invention.

A feed stream comprising 70 wt. % acetic acid and 21 wt. % ethyl acetate was fed to a Berty reactor in the presence of a hydrogenation catalyst comprising platinum, cobalt and tin on a modified silica support comprising cobalt, tin, and tungsten. Comparative Example B was fed to the reactor at a temperature of 225° C. Example 4 was fed to the reactor at a temperature of 250° C. Example 5 was fed to the reactor at a temperature of 275° C. Example 6 was fed to the reactor at a temperature of 300° C. The acetic acid conversion of each example is shown in FIG. 3. Selectivity of acetic acid to ethyl acetate for Comparative Example B and Examples 4-6 is shown in FIG. 4.

As can be seen in FIGS. 1-4, conversion of acetic acid increases as temperature increases and selectivity of the feed stream to ethyl acetate decreases as temperature increases.

While the invention has been described in detail, modifications within the spirit and scope of the invention will be readily apparent to those skilled in the art. All publications and references discussed above are incorporated herein by reference. In addition, it should be understood that aspects of the invention and portions of various embodiments and various features recited may be combined or interchanged either in whole or in part. In the foregoing descriptions of the various embodiments, those embodiments which refer to another embodiment may be appropriately combined with other embodiments as will be appreciated by one skilled in the art. Furthermore, those skilled in the art will appreciate that the foregoing description is by way of example only, and is not intended to limit the invention.

We claim:

1. A process for producing ethanol, comprising contacting hydrogen with a feed stream comprising acetic acid and/or ethyl acetate in a reactor at a temperature greater than 225° C. in the presence of a catalyst, under conditions effective to form ethanol, provided that the liquid hourly space velocity of the feed stream to the reactor is from 0.2 hr$^{-1}$ to 1 hr$^{-1}$, wherein the catalyst comprises a precious metal and one or more active metals on a modified support, wherein the modified support comprises (i) support material, and (ii) a support modifier comprising a metal selected from the group consisting of tungsten, molybdenum, vanadium, niobium and tantalum, and further wherein the one or more active metals are selected from the group consisting of copper, iron, cobalt, vanadium, nickel, titanium, zinc, chromium, molybdenum, tungsten, tin, lanthanum, cerium, manganese and mixtures thereof.

2. The process of claim 1, wherein the temperature is from 250° C. to 300° C.

3. The process of claim 1, wherein the liquid hourly space velocity of the feed stream fed to the reactor is from 0.2 to 0.8 hr$^{-1}$.

4. The process of claim 1, wherein the temperature is at least 250° C. and the liquid hourly space velocity of the feed stream fed to the reactor is from 0.3 to 1 hr$^{-1}$.

5. The process of claim 4, wherein conversion of acetic acid is at least 60%.

6. The process of claim 1, wherein the temperature is at least 275° C. and the liquid hourly space velocity of the feed stream fed to the reactor is from 0.3 to 1 hr$^{-1}$.

7. The process of claim 6, wherein conversion of acetic acid is at least 80%.

8. The process of claim 1, wherein the temperature is at least 300° C. and the liquid hourly space velocity of the feed stream fed to the reactor is from 0.3 to 1 hr$^{-1}$.

9. The process of claim 8, wherein conversion of acetic acid is at least 85%.

10. The process of claim 1, wherein acetic acid selectivity to ethanol is greater than 60 mol. %.

11. The process of claim 1, wherein the precious metal is selected from the group consisting of rhodium, rhenium, ruthenium, platinum, palladium, osmium, iridium and gold.

12. The process of claim 1, wherein the one or more active metals comprise cobalt and tin.

13. The process of claim 1, wherein the precious metal is present in an amount from 0.1 to 5 wt. %, and the one or more active metals comprise a second metal and a third metal, wherein the second metal is present in an amount from 0.5 to 20 wt. % and the third metal is present in an amount from 0.5 to 20 wt. %, based on the total weight of the catalyst.

14. The process of claim 1, wherein the precious metal is platinum and the one or more active metals comprise cobalt and tin; and further wherein the platinum is present in an amount from 0.1 to 5 wt. %, the cobalt is present in an amount from 0.5 to 20 wt. % and the tin is present in an amount from 0.5 to 20 wt. %, based on the total weight of the catalyst.

15. The process of claim 1, wherein the precious metal is palladium and the one or more active metals comprise cobalt and tin; and further wherein the palladium is present in an amount from 0.1 to 5 wt. %, the cobalt is present in an amount from 0.5 to 20 wt. % and the tin is present in an amount from 0.5 to 20 wt. %, based on the total weight of the catalyst.

16. The process of claim 1, wherein the support modifier comprises tungsten oxide.

17. The process of claim 1, wherein the support modifier comprises tungsten as a tungstate of cobalt.

18. The process of claim 1, wherein the support material is selected from the group consisting of silica, alumina, titania, silica/alumina, pyrogenic silica, high purity silica, zirconia, carbon, zeolites and mixtures thereof.

19. The process of claim 1, wherein the acetic acid is derived from a carbonaceous material selected from the group consisting of oil, coal, natural gas and biomass.

20. A process for producing ethanol, comprising contacting hydrogen with a mixed feed stream comprising acetic acid and ethyl acetate in a reactor at a temperature from greater than 225° C. to 300° C. in the presence of a catalyst, wherein the liquid hourly space velocity of the feed stream to the reactor is from 0.2 hr$^{-1}$ to 1 hr$^{-1}$, to form ethanol and achieve steady state ethyl acetate concentration, wherein the catalyst comprises a precious metal and one or more active metals on a modified support, wherein the modified support comprises (i) support material, and (ii) a support modifier comprising a metal selected from the group consisting of tungsten, molybdenum, vanadium, niobium and tantalum, and further wherein the one or more active metals are selected from the group consisting of copper, iron, cobalt, vanadium, nickel, titanium, zinc, chromium, molybdenum, tungsten, tin, lanthanum, cerium, manganese and mixtures thereof.

* * * * *